(12) United States Patent
Michaelis

(10) Patent No.: US 8,986,258 B2
(45) Date of Patent: Mar. 24, 2015

(54) DEVICE FOR RECEIVING A HYPODERMIC SYRINGE AND HYPODERMIC SYRINGE FOR THIS DEVICE

(71) Applicant: Gerresheimer Regensburg GmbH, Regensburg (DE)

(72) Inventor: Ina Michaelis, Schwandorf (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 0 days.

(21) Appl. No.: 13/932,826

(22) Filed: Jul. 1, 2013

(65) Prior Publication Data
US 2014/0005609 A1    Jan. 2, 2014

(30) Foreign Application Priority Data

Jul. 2, 2012   (DE) .......................... 10 2012 105 843

(51) Int. Cl.
  *A61M 5/32*  (2006.01)
  *A61M 5/31*  (2006.01)
  *A61M 5/315* (2006.01)

(52) U.S. Cl.
  CPC ................ *A61M 5/31* (2013.01); *A61M 5/326* (2013.01); *A61M 5/31511* (2013.01); *A61M 2005/3263* (2013.01)
  USPC ...................................... 604/198

(58) Field of Classification Search
  USPC ....................................... 604/198
  See application file for complete search history.

(56) References Cited

U.S. PATENT DOCUMENTS

| | | | | |
|---|---|---|---|---|
| 1,921,034 A | * | 8/1933 | La Marche | 604/157 |
| 4,631,057 A | * | 12/1986 | Mitchell | 604/198 |
| 4,723,943 A | * | 2/1988 | Spencer | 604/198 |
| 4,927,416 A | * | 5/1990 | Tomkiel | 604/198 |
| 4,929,237 A | * | 5/1990 | Medway | 604/198 |
| 5,106,379 A | * | 4/1992 | Leap | 604/198 |
| 5,855,839 A | * | 1/1999 | Brunel | 264/524 |
| 6,569,115 B1 | * | 5/2003 | Barker et al. | 604/110 |
| 6,719,730 B2 | * | 4/2004 | Jansen et al. | 604/192 |

(Continued)

FOREIGN PATENT DOCUMENTS

| | | |
|---|---|---|
| DE | 600 09 534 T2 | 6/2005 |
| DE | 602 25 540 T2 | 3/2009 |

OTHER PUBLICATIONS

Examination Report dated Apr. 15, 2013, from the German Patent Office for German Patent Application No. 10 2012 105 843.1.

*Primary Examiner* — Nicholas Lucchesi
*Assistant Examiner* — Diva K Chander
(74) *Attorney, Agent, or Firm* — Lathrop & Gage LLP

(57) ABSTRACT

A device for receiving a hypodermic syringe comprises an outer housing which has at one end a supporting element with an opening for an injection cannula and which has on its inner surface fixing means for engaging in counter-fixing means which are arranged on the outer surface of an injection container, and a displacement element which has at its end opposite the supporting element an actuating element on which at least one means is arranged which, during displacement, tensions a spring element with the build-up of a restoring force and, if a hypodermic syringe is received in the device, disengages the fixing means from the counter-fixing means. The spring element is disposed such that the outer housing and the injection container are moved relative to one another by the restoring force to such an extent until the injection cannula is fully received in the outer housing.

14 Claims, 6 Drawing Sheets

(56) References Cited

U.S. PATENT DOCUMENTS

Figure 1:
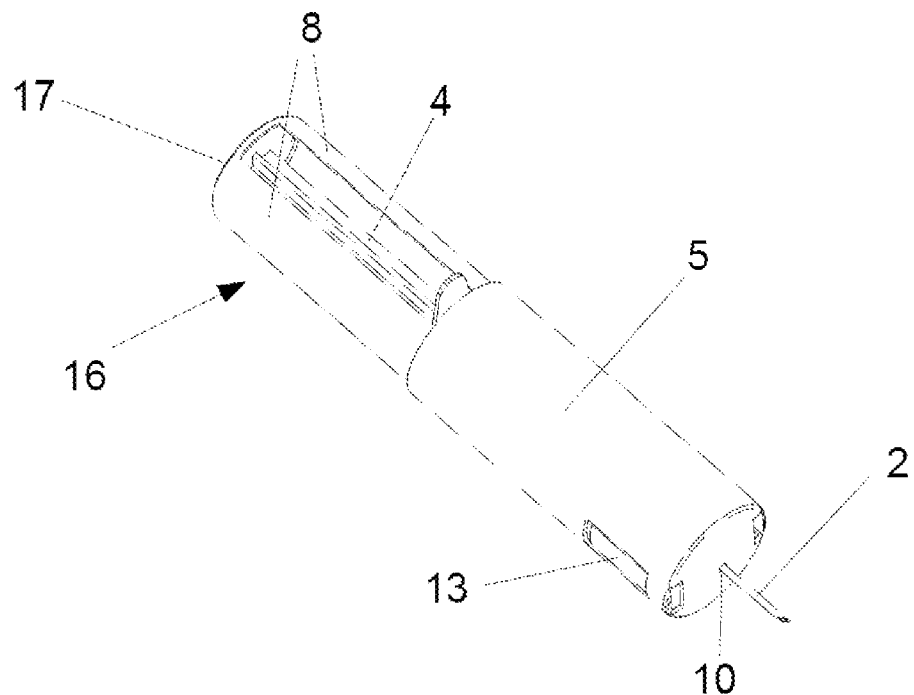

| | | | |
|---|---|---|---|
| 6,966,898 B1 * | 11/2005 | Pouget et al. | 604/197 |
| 7,582,073 B2 * | 9/2009 | Barrelle et al. | 604/192 |
| 7,699,814 B2 * | 4/2010 | Lande | 604/198 |
| 7,824,379 B2 * | 11/2010 | Doyle | 604/198 |
| 2006/0264887 A1 * | 11/2006 | Lande | 604/500 |
| 2012/0022465 A1 * | 1/2012 | Stamp et al. | 604/198 |

* cited by examiner

DEVICE FOR RECEIVING A HYPODERMIC SYRINGE AND HYPODERMIC SYRINGE FOR THIS DEVICE

CROSS-REFERENCE TO RELATED APPLICATIONS

This application claims the benefit of priority from German Application No. 10 2012 105 843.1, filed Jul. 2, 2012, which is hereby incorporated by reference in its entirety.

DESCRIPTION

The invention relates to a device for receiving a hypodermic syringe and to a hypodermic syringe for a device of this type.

In daily medical practice, hypodermic syringes are used in many cases for injecting medicines and other liquids into the human and animal body. They are also used for removing blood from human and animal bodies. When syringes are used, there is always the danger that the user could sustain a puncture wound with the tip of the cannula. When hypodermic syringes have not actually been used medically, the puncture wound itself is the greatest problem since the tip of the cannula is sterile from production, whereas when syringes have been used, the high risk of being infected with diseases possibly suffered by the person or animal being treated is the prevailing problem, since particles of blood from the person or animal being treated continue to adhere to the tip of the cannula after use. In this respect, used hypodermic syringes present a high risk of infection in health care as a whole.

A safety device for hypodermic syringes is already known from DE 600 09 534 T2, in which a hypodermic syringe is received in a housing, wherein an already compressed helical spring is prestressed or compressed before the actuation of the tip, and thus already has a restoring force. After the actuation of the hypodermic syringe or after the injection procedure, this prestress of the helical spring is released, such that the helical spring is displaced into the housing by the restoring force of the helical spring to such an extent that the hypodermic needle is completely covered in the longitudinal extension thereof by the housing. However, since the helical spring is already received in a prestressed manner in the housing of the device before the actuation of the hypodermic syringe, there is a risk that, due to the material, said spring will decompress at least in part in the time period between the production of this device and the injection. In the event of such a decompression of the helical spring, the hypodermic needle would not at least be covered completely in the longitudinal extension thereof by the housing, and as a result, there would still be a risk of potential puncture wounds.

DE 602 25 540 T2 also describes a similar device, in which likewise a prestressed helical spring is used, such that also in the case of this device, the prestressed helical spring can become fatigued due to the material. In this case as well, the hypodermic needle would not at least be covered completely in the longitudinal extension thereof by the housing after the use or actuation of the hypodermic syringe, and as a result, there would still be a risk of potential puncture wounds.

It is therefore the object of the invention to provide a device for receiving a hypodermic syringe, as well as a hypodermic syringe for a device of this type which can advantageously be used for the injection and removal of media, the risk of puncture wounds being virtually ruled out after the hypodermic syringe has been used, and a safe operation for preventing puncture wounds being ensured.

This object is achieved by a device having all the features of claim 1 and by a hypodermic syringe having all the features of claim 7. Advantageous configurations of the invention are presented in the subclaims.

The device according to the invention for receiving a hypodermic syringe comprises an outer housing which has at one end a supporting element with an opening for an injection cannula of the hypodermic syringe and which has on its inner surface fixing means for engaging in counter-fixing means arranged on the outer surface of an injection container of the hypodermic syringe. The device also comprises a displacement element which can be arranged in a captively displaceable manner in the outer housing and which has at its end opposite to the supporting element an actuating element on which at least one means is arranged which, during displacement of the displacement element in the outer housing, tensions at least one spring element with the build-up of a restoring force and, if a hypodermic syringe is accommodated in the device, disengages the fixing means from the counter-fixing means of the hypodermic syringe and the at least one spring element is disposed such that the outer housing and the injection container are displaced towards one another, relative to one another, by the restoring force to such an extent until the injection cannula is fully received in the outer housing, wherein the at least one spring element is configured as a substantially sinusoidal spring element or as a spiral spring element or the like, which consists of plastics material.

The relative displacement of the outer housing and of the injection container towards one another takes place in that, after the actuation of a hypodermic syringe introduced into the device according to the invention, the outer housing and the displacement element are moved relative to one another in a translatory manner by the restoring force of the spring element, said force being built up by the actuation of the hypodermic syringe, while the injection container of the hypodermic syringe is held in the displacement element and is displaced with the displacement element.

This configuration of the device according to the invention ensures that after the device according to the invention has been used with a hypodermic syringe received therein, the injection cannula of the hypodermic syringe is received in an automated manner into the outer housing of the device, thereby reliably preventing puncture wounds after the hypodermic syringe has been used and preventing possible infections as a result of the blood residues of the treated patient, adhering to the injection cannula. The device according to the invention provides a simple construction of a safety device of this type which is also characterised by low costs in terms of material and production. Since the spring element for generating the restoring force only generates said restoring force upon actuation of the hypodermic syringe by the displacement element, in addition to the safety aspects, a device with the hypodermic syringe accommodated therein is also provided in which, when unused, no restoring force acts on elements of the device according to the invention or on the hypodermic syringe. An unintentional initiation of an injection procedure is avoided thereby, because no force is acting on the plunger of the hypodermic syringe. In addition, a faultless operation of the device according to the invention is ensured in that, in the unstressed state, the spring element cannot sustain any material fatigue, which would result in a potentially insufficient restoring force.

According to a first advantageous configuration of the invention, means are provided for inhibiting a displacement of the displacement element in the direction of the supporting element when the restoring force has displaced the displacement element to such an extent that the injection cannula has been fully received by the outer housing, if a hypodermic syringe has been received in the device, these means preferably being configured as snap-in hooks or the like. This measure prevents the injection cannula, received in the outer housing after use, from being able to be displaced out of the outer housing again. In this respect, it is unnecessary to further take measures for storing used injection cannulas. Once the injection cannula has been received in the outer housing, it is no longer possible to make the cannula freely accessible again through the opening in the outer housing. Thus, separate storage containers are actually no longer necessary, although they might have to be used for regulatory reasons.

The fixing means are advantageously configured as snap-in hooks, or the like. The counter-fixing means are preferably configured, for example, as ramps or the like, which can either be configured in an integral construction with the injection container or can be built thereon. This measure makes it easily possible in terms of production to fix the inner housing in the outer housing.

In this respect, the means arranged on the actuating element are preferably configured as fingers and, when the plunger or the plunger feed element is moved on run-on slopes of the fixing elements of the outer housing or of the snap-in hooks there, said fingers run along such that they are disengaged from the counter-fixing means of the injection container or of the ramps there of a hypodermic syringe received in the device according to the invention. The fixing elements are pressed radially outwards by the fingers, thereby releasing the locking effect between the counter-fixing elements and the fixing elements and the displacement element or the injection container, now arranged therein, can thereby be displaced in the outer housing. However, since the displacement element is held captive in the outer housing, it cannot be released from the outer housing without the device being intentionally destroyed.

In order to be able to easily press the fixing elements, and in particular the snap-in hooks, configured as such, radially outwards, it has proved to be advantageous to arrange in the outer housing openings into which the fixing elements or the snap-in hooks can escape during displacement of the plunger or of the plunger feed element. In this respect, a great amount of force is not required to disengage the counter-fixing elements and the fixing elements.

As mentioned at the outset, the at least one spring element is configured as a sinusoidal spring element or as a spiral spring element or the like, which consists of plastics material. Spring elements of this type produced from plastics material are available in all possible strengths for very different restoring forces and can be fitted in a hypodermic syringe according to the invention by established methods. In this respect, the device is preferably configured with the hypodermic syringe already received therein such that in the starting position, in which the injection container is already filled with a medium, it contains the spring element in the relaxed state between the injection container of the hypodermic syringe and the outer housing of the device according to the invention. When the medium is injected, the plunger is moved towards the end of the injection container supported on the supporting element of the device by means of the plunger feed element which is actuated by the actuating element of the displacement element. In so doing, the fingers arranged on the actuating element of the displacement element impact the run-on slopes of the snap-in hooks of the outer housing and, as the plunger continues to move, release the injection container from the outer housing, so that the injection container, together with the displacement element, can be displaced inside the outer housing. At the same time, during the injection procedure, the spring element is tensioned by the fingers as a result of the movement of the plunger, possibly even before the injection container is released from the outer housing, and a restoring force is built up. Due to this restoring force of the spring element, the displacement element and the injection container contained therein can be displaced automatically in the outer housing, relative thereto. The displacement continues at least until the injection cannula has been completely received in the outer housing or until the outer housing has been pushed over the injection cannula and thus the injection cannula no longer presents any risk of puncture injury.

In order that the injection cannula also remains in the outer housing and is not simply pushed out of said housing again due to a pressing of the plunger feed element or of the actuating element of the displacement element, and thus is exposed again, it is provided that the means for inhibiting the plunger feed element are configured as snap-in hooks or the like, by which is it easily possible to produce an inhibiting action of this type.

According to a further idea of the invention, the outer housing has a curved path, in particular a restricted guidance for the displacement element or for the fingers arranged thereon, which restricted guidance prevents a backwards movement of the displacement element inside the outer housing.

The hypodermic syringe according to the invention for the previously described device is further characterised in that an injection container of the hypodermic syringe has counter-fixing means which are arranged on its outer surface and are preferably configured as ramps or the like and are an integral component of the injection container or can be built thereon. These are capable of cooperating with the fixing means, in particular with the fixing means of the device configured as snap-in hooks, such that the hypodermic syringe is fixed securely before the medium in the injection container is injected. Furthermore, these counter-fixing means can be easily disengaged from the fixing means of the device by the means, preferably configured as fingers, of the displacement element of the device.

In this respect, it has proved to be successful for the injection container of the hypodermic syringe to consist of a preferably transparent plastics material or of glass. Users and patients are accustomed to hypodermic syringes of this type and thus they are also perceived as familiar treatment agents and, during production, it is naturally also possible to revert to tested production methods.

According to a further idea of the invention, the injection container has a curved path, in particular a restricted guidance for the displacement element or for the fingers arranged thereon, which restricted guidance prevents a backwards movement of the displacement element from the distal end to the proximal end of the outer housing. This configuration is particularly advantageous if the previously described device does not have any means for a restricted guidance of this type.

Further objectives, advantages, features and possible uses of the present invention are provided in the following description of an embodiment with reference to the drawings. In this respect, all the described and/or illustrated features form on their own or in any meaningful combination the subject-matter of the present invention, also irrespective of their summarisation in the claims or of their reference thereto.

Figure 2:
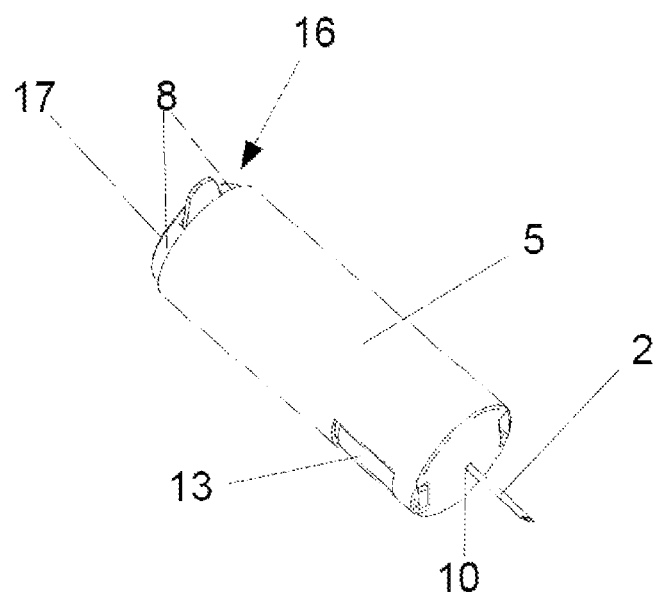
Figure 3:
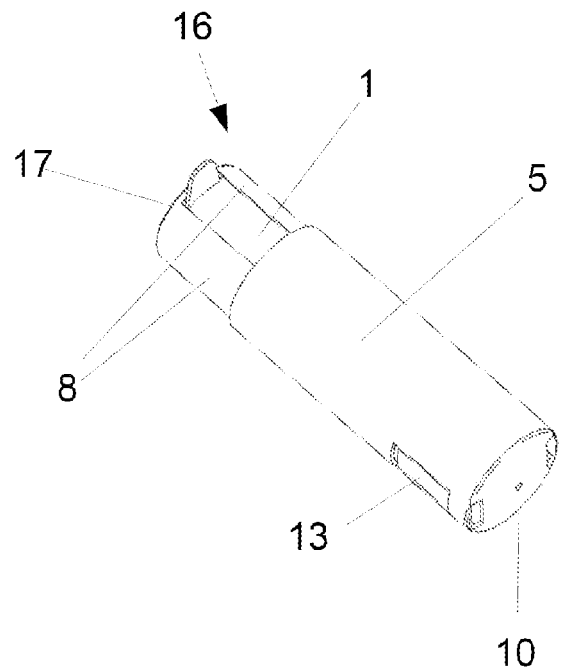
Figure 4:
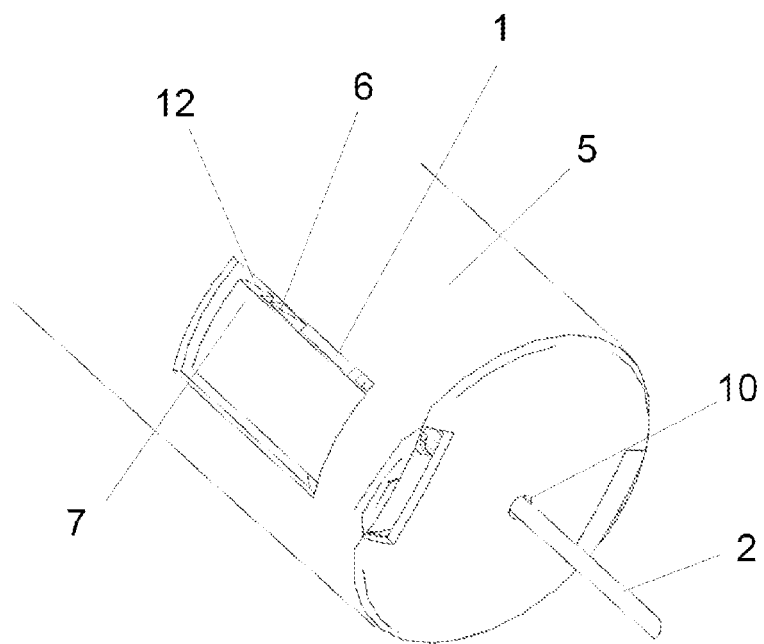
Figure 5:
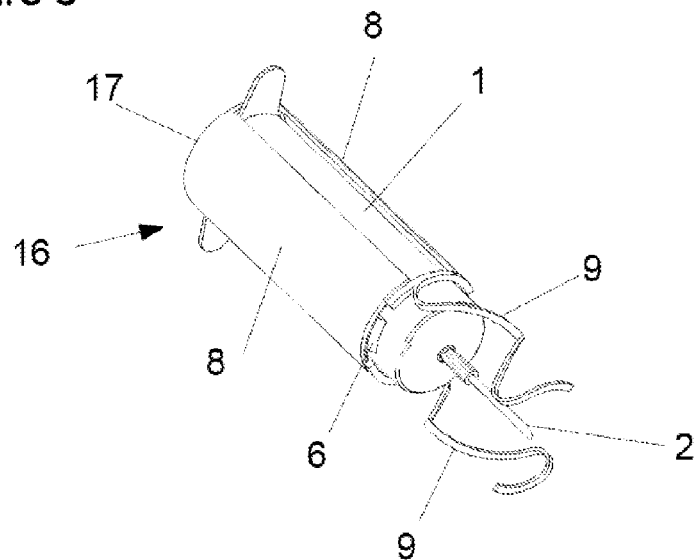
Figure 6:
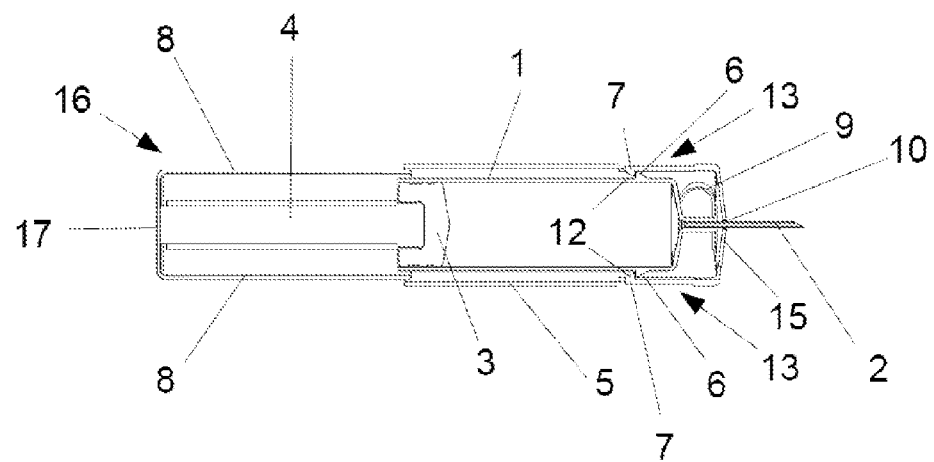
Figure 7:
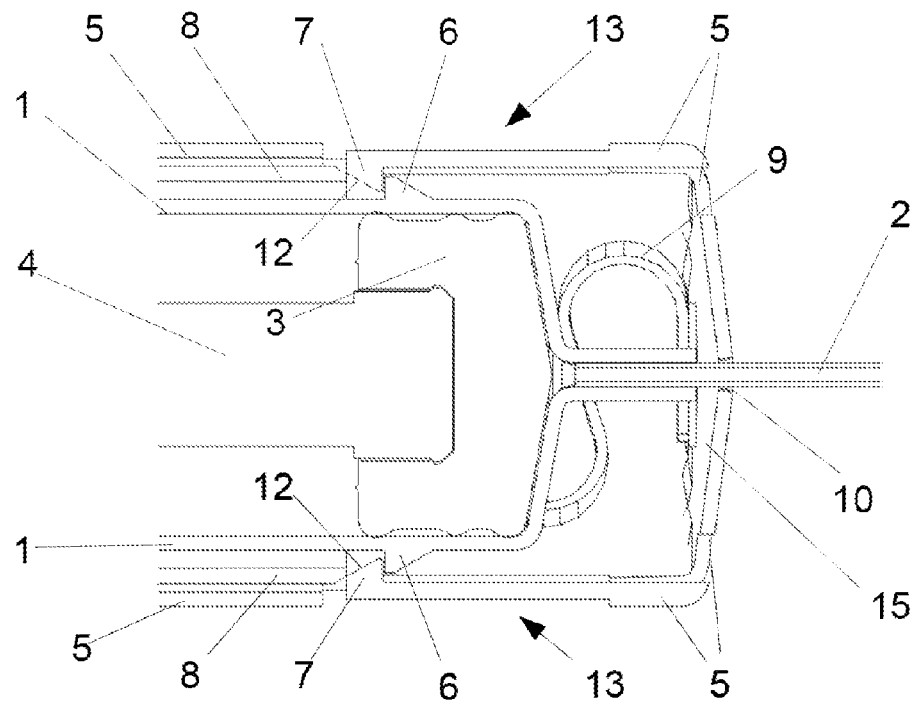
Figure 8:
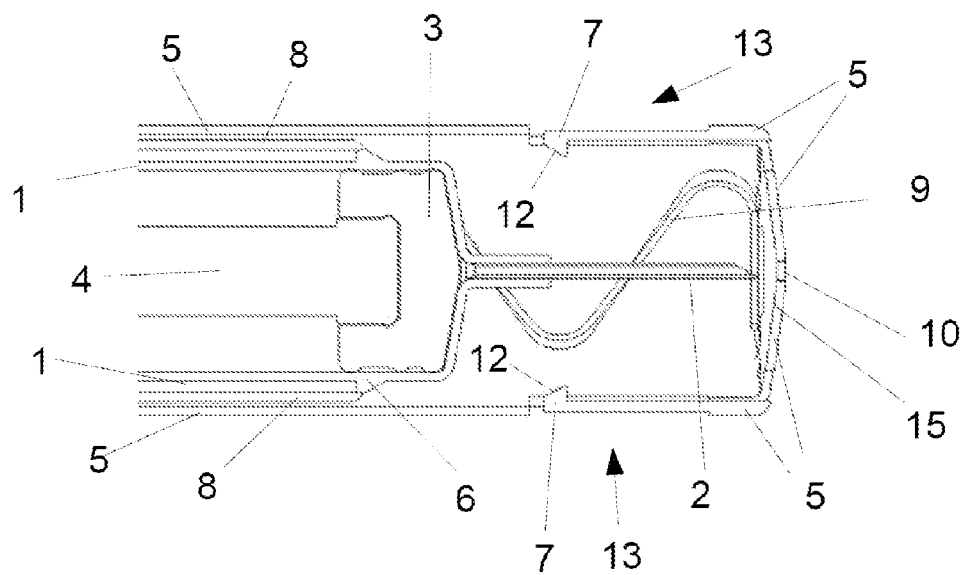
Figure 9:
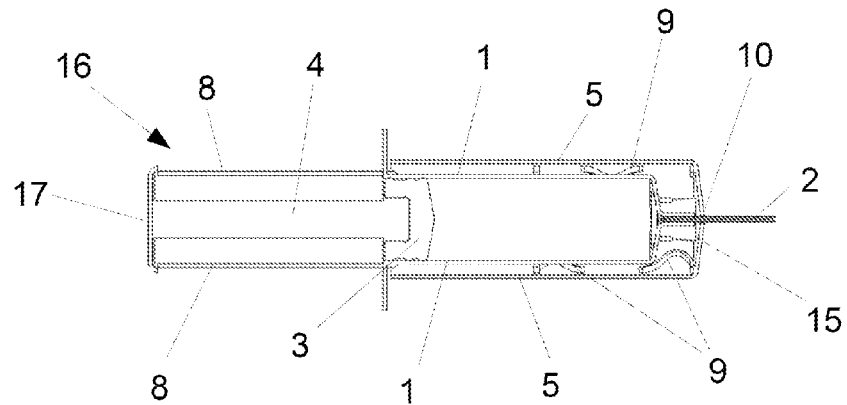
Figure 10:
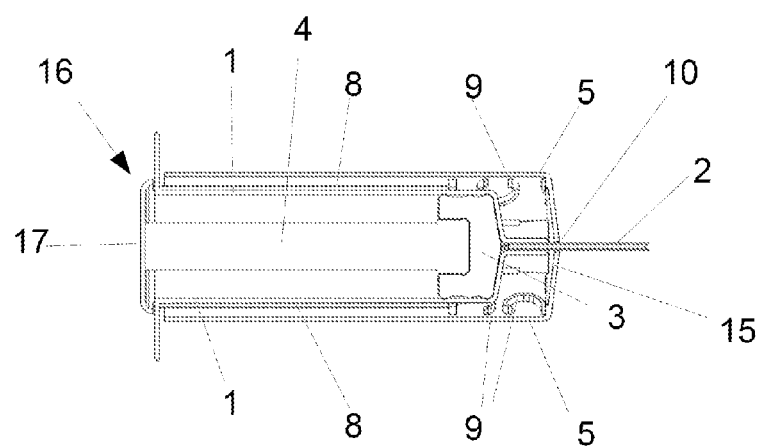
Figure 11:
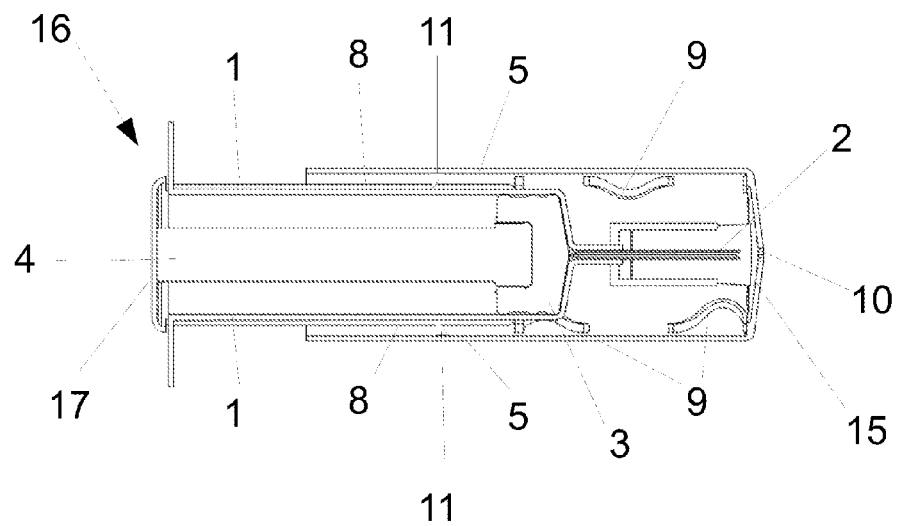

FIG. 1 shows an embodiment of a device according to the invention with a hypodermic syringe received therein, the plunger of the hypodermic syringe resting against an actuating element of the device and the injection container of the hypodermic syringe having been filled with a medium, FIG. 2 shows the embodiment according to FIG. 1, the plunger now however having been displaced to the end of the injection container resting against a supporting element of the device and the medium having been conveyed out of the injection container via the injection cannula, FIG. 3 shows the embodiment according to FIG. 1, the injection cannula of the hypodermic syringe being in a secured position after the injection procedure, FIG. 4 is a detailed illustration of FIG. 1 in the region of the end of the outer housing having a hypodermic needle, FIG. 5 is an illustration of a displacement element of the device according to the invention according to FIG. 1 together with a hypodermic syringe received therein and a sinusoidal plastics material spring element arranged thereon, FIG. 6 is a cross-sectional view of the embodiment according to FIG. 1, FIG. 7 is a detailed illustration of the cross-sectional view according to FIG. 6 in the region of the end of the device receiving an injection cannula, FIG. 8 is a cross-sectional detailed illustration of the embodiment according to FIG. 3 in the region of the end of the device receiving an injection cannula, FIG. 9 is a cross-sectional view of the embodiment according to FIG. 6, rotated by 90° about the longitudinal axis of the device, FIG. 10 is a cross-sectional view of the embodiment according to FIG. 2, and FIG. 11 is a cross-sectional view of the embodiment according to FIG. 3.

The figures show an embodiment of the device according to the invention in different views. In this respect, FIGS. 1, 6 and 9 show this embodiment of the device with a plunger 3 arranged at an end, opposite a supporting element 15, of an injection container 1 of a hypodermic syringe. The plunger 3 is in this position when the injection container 1 is filled with a medium which is to be injected into a patient. The plunger 3 can now be pushed manually by a user towards the end of the outer housing 5 having the supporting element 15 by means of a plunger feed element 4. As can be seen in FIG. 6, the injection container 1 is held and fixed on snap-in hooks 7 of the outer housing 5 by ramps 6 such that an injection cannula 2, arranged on the injection container 1, protrudes out of the outer housing 5 through an opening 10 in said outer housing so that the patient's skin can be punctured. The snap-in hooks 7 of the outer housing 5 are arranged on the same such that they are mounted resiliently and can move out of the outer housing 5 via openings 13.

When the patient's skin is punctured, the medium in the injection container 1 can be injected. For this purpose, the plunger 3 is moved from the end of the injection container 1 opposite the supporting element 15 towards the end of the injection container 1 resting against the supporting element 15 by the user of the hypodermic syringe by means of the plunger feed element 4 or by an actuating element 17, which moves the plunger feed element 4, of a displacement element 16. During this movement, a substantially sinusoidal spring element 9, which is supported on the supporting element 15 of the outer housing 5 and on the displacement element 16, is tensioned out of its relaxed starting position so that this spring element 9 causes a restoring force to act on the displacement element 16.

Furthermore, during the movement of the plunger 3 in the injection container 1, the fingers 8 arranged on the displacement element are also moved in the direction of the supporting element 15 between the injection container 1 and the outer housing 5. During this movement, the fingers 8 slide along run-on slopes 12 of the snap-in hooks 7 arranged on the outer housing 5 and press said snap-in hooks radially outwards into the openings 13, so that the snap-in hooks 7 of the outer housing 5 disengage from the ramps 6 of the injection container 1 and, in this moment, the injection procedure is substantially concluded. The injection container 1 is now no longer positioned fixedly inside the outer housing 5, but can be displaced in the same together with the displacement element 16. The injection procedure is now substantially concluded, the plunger 3 having displaced as far as the end of the injection container 1 located in the direction of the supporting element 15 by means of the plunger feed element 4 or by the actuating element 17, as shown in particular in FIGS. 2, 7 and 10. The spring element 9 is now also tensioned such that the maximum restoring force of the spring element 9 acts between the outer housing 5 and the displacement element 16 with the injection container 1 held therein.

Since the snap-in hooks 7 of the outer housing 5 and the ramps 6 of the injection container 1 are disengaged, the restoring force of the spring element 9 is able to displace the outer housing 5 as soon as the plunger feed element 4 is still only subjected to a lesser force than the restoring force of the spring element 9 or is no longer subjected to any force at all. At the end of this displacement procedure, the displacement element 16 with the injection container 1 held therein is located at the end of the outer housing opposite the supporting element 15. In this respect, the outer housing 5 moves over the injection cannula 2 and receives it completely. During this movement of the displacement element 16 with the injection container 1 held therein in the outer housing 5, the injection cannula 2 arranged on the injection container 1 is also displaced into the interior of the outer housing 5 until it is completely received therein, without the cannula continuing to protrude out of the opening 10 in the outer housing 5.

The injection cannula 2 is now secured in this state and can no longer cause any puncture wounds. The displacement element 16 with the injection container 1 held therein is preferably displaced in the outer housing 5 such that it is no longer possible for the injection container 1 to move in the direction of the end of the outer housing having the supporting element. After use, the injection cannula 2 is thus stored securely in the outer housing 5 and can no longer exit the outer housing 5 without this housing being destroyed. This secured end position is shown in different views in FIGS. 3, 8 and 11.

FIGS. 4, 6, 7 and 8 show a more detailed illustration of the ramps 6 of the injection container 1 and of the snap-in hooks 7 of the outer housing 5, and of the cooperation thereof.

FIG. 5 shows the described embodiment without an outer housing 5, thus allowing a clear view in particular of the arrangement of the spring element 9 and the cooperation thereof with the fingers 8 of the displacement element 15 or of the displacement element 15 itself and also with the injection container 1, arranged in the displacement element 15, or with the hypodermic syringe.

FIG. 11 also shows snap-in hooks 11 which prevent the displacement element 16 from being able to be displaced again in the direction of the supporting element 15 inside the outer housing 5. This ensures that the injection cannula 2 cannot be guided again out of the outer housing 5 through the opening 10.

The actuating element 17 has on its surface facing the supporting element 15 a connection element, preferably an adhesive-containing element, using which it is possible to attach the plunger feed element 4 to the actuating element 17 and thereby to the displacement element 16. This ensures that the spring element 9 not only produces by its restoring force a relative movement between outer housing 5 and displacement element 16. In fact, due to the connection between displacement element 16 and plunger feed element 4, the injection container 1 is also always jointly moved at the same time, so that the injection container 1 also jointly performs the relative movement between outer housing 5 and displacement element 16. This ensures that in any case, the outer housing 5 securely receives the injection cannula 2 of the hypodermic syringe.

LIST OF REFERENCE NUMERALS

1 injection container
2 injection cannula
3 plunger
4 plunger feed element
5 outer housing
6 counter-fixing means, ramp
7 fixing means, snap-in hooks
8 means, fingers
9 spring element
10 opening
11 means, snap-in hooks
12 run-on slopes
13 opening
15 supporting element
16 displacement element
17 actuating element

The invention claimed is:

1. A device for receiving a hypodermic syringe comprising an outer housing which has at one end a supporting element with an opening for an injection cannula of the hypodermic syringe and which has on its inner surface fixing means for engaging in counter-fixing means which are arranged on the outer surface of an injection container of the hypodermic syringe, and comprising a displacement element which can be arranged in a captively displaceable manner in the outer housing and which has at its end opposite the supporting element an actuating element on which at least one means is arranged which, during displacement of the displacement element in the outer housing, tensions at least one spring element with the build-up of a restoring force and, if a hypodermic syringe is received in the device, disengages the fixing means from the counter-fixing means of the hypodermic syringe and the at least one spring element is disposed such that the outer housing and the injection container are moved relative to one another by the restoring force to such an extent until the injection cannula is fully received in the outer housing, wherein the at least one spring element is formed as a substantially sinusoidal spring element or as a spiral spring element or the like, which consists of plastics material.

2. The device according to claim 1, wherein means for inhibiting a displacement of the displacement element in the direction of the supporting element are provided when the restoring force has displaced the displacement element to such an extent that the injection cannula has been fully received by the outer housing if a hypodermic syringe has been received in the device.

3. The device according to claim 1, wherein the fixing means are configured as snap-in hooks.

4. The device according to claim 1, wherein the means on the actuating element are configured as fingers, which fingers run along run-on slopes of the fixing means when the displacement element is displaced.

5. The device according to claim 4, wherein arranged in the outer housing are openings into which the fixing means can escape during displacement of the displacement element.

6. The device according to claim 1, wherein the outer housing has a curved path with a restricted guidance for the displacement element, which restricted guidance prevents a backwards movement of the displacement element inside the outer housing.

7. The hypodermic syringe for a device according to claim 1, wherein the injection container of the hypodermic syringe has counter-fixing means which are arranged on its outer surface and are configured as ramps.

8. The hypodermic syringe according to claim 7, wherein the injection container consists of a transparent plastics material or of glass.

9. The hypodermic syringe according to claim 7, wherein the injection container has a curved path with a restricted guidance for the displacement element, which restricted guidance prevents a backwards movement of the displacement element inside the outer housing.

10. The hypodermic syringe according to claim 8, wherein the injection container has a curved path with a restricted guidance for the displacement element, which restricted guidance prevents a backwards movement of the displacement element inside the outer housing.

11. The device according to claim 2, wherein the means for inhibiting a displacement of the displacement element in the direction of the supporting element are configured as snap-in hooks.

12. The device according to claim 4, wherein the outer housing has a curved path with a restricted guidance for the fingers on the displacement element, which restricted guidance prevents a backwards movement of the displacement element inside the outer housing.

13. The device according to claim 5, wherein the fixing means are configured as snap-in hooks.

14. The device according to claim 1, wherein the spring and the displacement element are a unitary body.

* * * * *